United States Patent
Rothschild

(10) Patent No.: US 11,205,503 B2
(45) Date of Patent: *Dec. 21, 2021

(54) DRUG SUBSTANCE INTERACTION AND GENERIC SUBSTANCE INFORMATION RETRIEVAL

(71) Applicant: SRR PATENT HOLDINGS, LLC, Cheyenne, WY (US)

(72) Inventor: Leigh M. Rothschild, Sunny Isles Beach, FL (US)

( * ) Notice: Subject to any disclaimer, the term of this patent is extended or adjusted under 35 U.S.C. 154(b) by 241 days.

This patent is subject to a terminal disclaimer.

(21) Appl. No.: 15/803,919

(22) Filed: Nov. 6, 2017

(65) Prior Publication Data

US 2018/0060526 A1 Mar. 1, 2018

Related U.S. Application Data

(60) Division of application No. 13/645,086, filed on Oct. 4, 2012, now Pat. No. 9,836,582, which is a continuation-in-part of application No. 13/408,008, filed on Feb. 29, 2012, now abandoned, which is a continuation of application No. 12/191,759, filed on Aug. 14, 2008, now Pat. No. 8,155,887.

(51) Int. Cl.
*G16C 20/80* (2019.01)
*G16H 20/10* (2018.01)
*G16H 70/40* (2018.01)

(52) U.S. Cl.
CPC ............. *G16C 20/80* (2019.02); *G16H 20/10* (2018.01); *G16H 70/40* (2018.01)

(58) Field of Classification Search
CPC ........... G06K 9/00671; G06K 9/00771; G06K 9/00624; G06K 2209/01; G06K 9/325; G06K 9/00718; G06K 2209/21; G06K 2209/25; G06K 9/0014; G06K 9/00147; G06K 9/00208; G06K 9/00288; G06K 9/20; G06K 9/2081; G06K 9/3241; G06K 9/6202; G06K 9/6218; G06K 9/6227; G16H 50/20; G16H 10/60; G16H 40/63; G16H 20/10; G16H 30/40; G16H 40/20; G16H 50/70; G16H 10/40; G16H 20/13; G16H 40/67; G16H 70/40; G06Q 10/087; G06Q 20/203; G06Q 30/06; G06Q 50/24; G06Q 20/322; G06T 2207/30004; G06T 5/20; G06T 7/0014; G06T 7/97; G06T 7/32; G06T 7/73; G06T 7/74; G06T 7/90; G06F 16/55; G06F 16/90335; G06F 3/0482; G06F 19/00; G06F 19/326; G06F 19/3456; G06F 16/53; G06F 19/325; G06F 19/328; G06F 1/163; G06F 1/1686; G06N 5/02; G02B 2027/0138; G02B 2027/014; G02B 2027/0141; G16B 20/00; G16B 25/00; G16B 30/00; G01N 2500/00; G01N 37/00; G01N 2035/0091; G01N 2035/00702; G01N 2021/0181; G01N 2021/0112; G01N 2021/0106; Y10T 436/113332; G16C 20/80
See application file for complete search history.

(56) References Cited

U.S. PATENT DOCUMENTS

| | | |
|---|---|---|
| 815,887 A | 3/1906 | Woodbury |
| 7,154,102 B2 | 12/2006 | Poteet et al. |
| 7,469,213 B1 | 12/2008 | Rao |
| 7,747,454 B2 * | 6/2010 | Bartfeld .............. G06F 19/3462 705/3 |
| 7,860,603 B2 * | 12/2010 | Handfield ............... G07F 9/026 700/236 |
| 9,836,582 B2 * | 12/2017 | Rothschild ............. G16C 20/80 |
| 10,262,107 B1 * | 4/2019 | Tran ....................... G06N 20/00 |
| 10,552,575 B1 * | 2/2020 | Mohebbi .............. G06K 9/4609 |
| 2002/0021828 A1 * | 2/2002 | Papier ................... G06F 19/324 382/128 |
| 2012/0163685 A1 | 6/2012 | Rothschild |
| 2012/0253829 A1 * | 10/2012 | John ...................... G06Q 50/22 705/2 |
| 2013/0028480 A1 | 1/2013 | Rothschild |
| 2014/0052555 A1 * | 2/2014 | MacIntosh ........... G06Q 20/208 705/23 |

* cited by examiner

*Primary Examiner* — Mary K Zeman

(57) ABSTRACT

A data processing system configured for computer visualization of drugs for drug interaction information retrieval is disclosed. For each of multiple different substances and using a camera within the mobile or other computing device, imagery of at least one external characteristic of a physical body of the substance is acquired. An identity of each of the multiple different substances is determined based upon the at least one external characteristic from the acquired imagery. Drug interaction data is retrieved for each of the multiple different substances using the determined identities. Drug interaction data for at least one of the multiple different substances is correlated with at least one other of the multiple different substances. At least one generic substance and/or cost information of at least one of the multiple different substances is identified. The correlated drug interaction data, the at least one generic substance, and/or the cost information are displayed.

10 Claims, 3 Drawing Sheets

DRUG SUBSTANCE INTERACTION AND GENERIC SUBSTANCE INFORMATION RETRIEVAL

CROSS-REFERENCE TO RELATED APPLICATIONS

This application is a divisional application of U.S. application Ser. No. 13/645,086, filed on Oct. 4, 2012, which is a Continuation-in-Part of U.S. application Ser. No. 13/408,008, filed on Feb. 29, 2012, which is a is a Continuation of U.S. application Ser. No. 12/191,759, filed on Aug. 14, 2008, all of which are incorporated herein by reference in their entirety.

BACKGROUND

1. Field

The present invention relates to the field of computerized drug identification and more particularly to computer aided visualization for drug identification.

2. Description of the Related Art

Prescription drug use has become part and parcel of modern society. Though medicinal compositions have always been dispensed for what ails and even for what does not ail, governmental regulation of food and drugs in recent years has resulted in the consolidation of medicinal compositions into two classes of drugs—those that require a prescription and those that do not. Recent advances in technology have made available many drugs formerly requiring a prescription as "over-the-counter" medications requiring no prescription at all. In many cases, over-the-counter versions of a prescription drug are no more than weakened forms of the prescription drug. In any event, the widespread availability of drugs, both prescription and over-the-counter, has resulted in a substantial population of patients consuming multiple different types of drugs at any given time.

Drug interactions remain a principal aspect of the pharmaceutical sciences. A drug interaction is a commonly known situation in which a substance affects the activity of a drug, such that the effects of a given drug is increased or decreased, or the combination of the substance and the drug produce a new effect that neither produces alone. Typically, drug-drug interactions are most unpredictable; however, drug-food interactions also are known to exist between drugs and foods, as well as drug-herb interactions between drugs and herbs.

Generally speaking, it is desirable to avoid drug interactions due to the possibility of a poor or unexpected outcome resulting from the interaction of a drug with another substance. Consequently, known drug interactions often are listed in the literature distributed with a drug. Providing an exhaustive list of drug interactions in literature, however, can be difficult when a substantial number of drug interactions are known to exist. As such, voluminous books have been created as an aggregation of known drug interactions. While the most diligent review of a book of known drug interactions will reveal the requisite information necessary to avoid an undesirable outcome from a drug interaction of a prescribed selection of drugs, in practice it is not reasonable to presume that a dispensary of drugs will consult the requisite literature when dispensing a drug.

Further, for each drug, there may be one or more substances comparable in dosage form, strength, route of administration, quality and performance characteristics, and intended use. Such substances are known as generic substances or generics, which are usually sold at significantly lower prices than their brand name drug equivalents. However, the average consumer may not be aware of the full range of generic drugs available. Moreover, the average consumer may not be able to readily access pricing information for drugs and generic substances to make informed and/or cost-effective decisions on their purchases.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION

The present disclosure describes a method, system and computer program product for computer visualization of drugs for drug interaction, generic substance and/or cost information retrieval. In accordance with the present disclosure, multiple different drugs can be imaged to detect identifiable content disposed on the different drugs. Each image of each drug can be compared to a data store of drug information to identify each drug. Thereafter, drug interaction, generic substance and/or cost data can be retrieved for each identified drug. Further, known drug-drug interactions, generic alternatives and/or cost information for the identified drugs can be determined and one or more reports can be provided to include the known drug-drug interactions, generic alternatives and/or cost information. In this way, drug-drug interactions resulting from the use of the multiple different drugs can be determined without recourse to a voluminous text of drug interactions. Alternatively, or in addition, any known generic substances for each identified drug can be determined. Still alternatively or in addition, known pricing information associated with each identified drug and/or generic substance can be determined.

Figure 1:
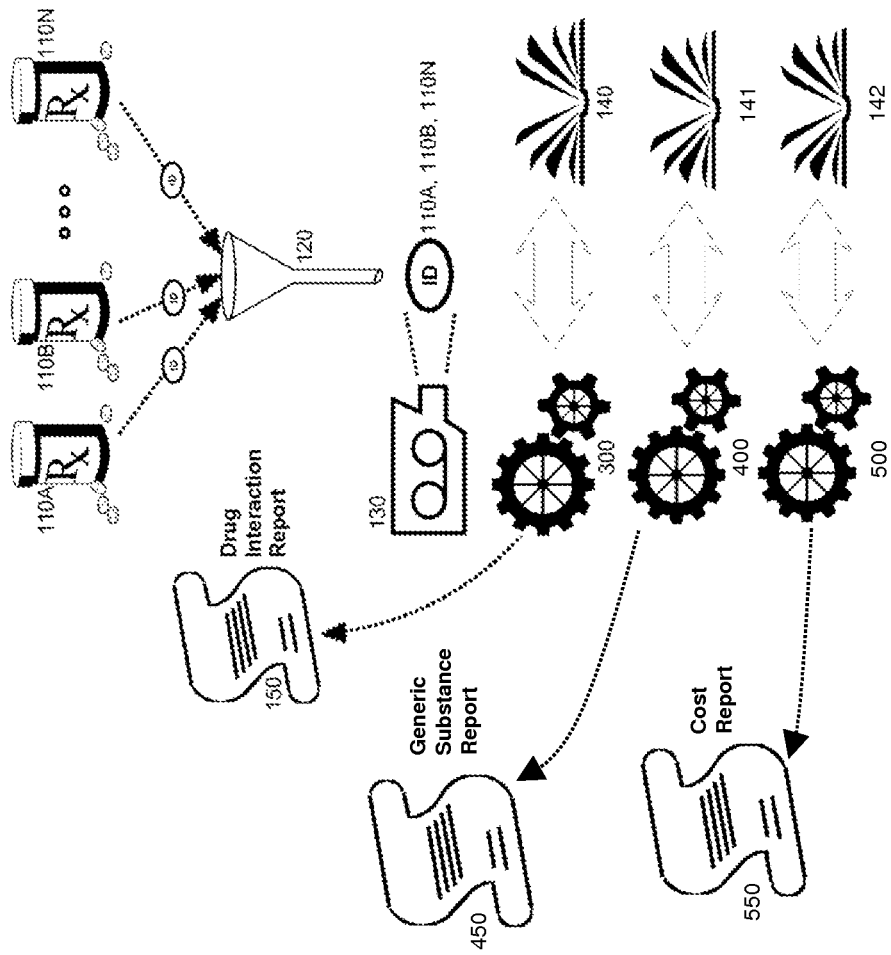
FIG. 1 is a pictorial illustration of a process for computer visualization of drugs for drug interaction, generic substance and/or cost information retrieval.

In illustration, FIG. 1 is a pictorial illustration of a process for computer visualization of drugs for drug interaction, generic substance and/or cost information retrieval. As shown in FIG. 1, multiple different substances 110A, 110B, 110N, whether prescription drugs, over-the-counter drugs or even vitamins and herbal remedies, can optionally be provided to a marshalling apparatus 120 such as a gravity feed or miniature conveyor belt or even a chamber. The marshalling apparatus 120 can isolate an individual one of the different substances 110A, 110B, 110N for imaging by camera 130, for example a charge coupled device (CCD) driven still or video camera.

In certain aspects, the camera 130 is contained within a mobile computing device. The mobile computing device can be, for example, a smart phone, a personal digital assistant, a tablet computer, a laptop computer, a portable communication device, iPod™, etcetera. The mobile computing device can be configured to communicate via a wireless or wired medium. The mobile computing device can include any suitable operating system, including Android, iOs, Windows, BlackBerry OS, Symbian IS, bada, webOS, GridOS, Mer project, SHR, MeeGo, Linux, Brew, and/or LiMo, just to name a few possibilities.

The camera 130 can capture an image of each individual one of the different substances 110A, 110B, 110N and computer visualization for drug interaction information retrieval logic 300 can process each captured image to detect identifying content disposed on each of the different substances 110A, 110B, 110N such as a pill marking or code.

The computer visualization for drug interaction information retrieval logic 300 in turn can compare the identified content to a data store of known substances 140 to identify each of the different substances 110A, 110B, 110N. The computer visualization for drug interaction information retrieval logic 300 further can lookup not only known drug interactions for each of the different substances 110A, 110B, 110N, but also known drug interactions between the identified ones of the substances 110A, 110B, 110N. Thereafter, a drug interaction report 150 can be produced indicating the known drug interactions between the identified ones of the substances 110A, 110B, 110N.

Additionally and/or alternatively, generic drug retrieval logic 400 can compare the identified content to a data store of known generic substances 141 to identify any possible generics for each of the different substances 110A, 110B, 110N. A "generic substance" is any natural or man-made product, substance or item that is identical or within an acceptable range to a given drug in dosage form, strength, route of administration, quality and performance characteristics, and/or intended use. The generic substance can include at least the authorized generic drugs or substances approved by the U.S. Food and Drug Administration and/or by any other domestic or foreign government or non-governmental agency, entity, organization or individual. Thereafter, a generic drug report 450 can be produced indicating any known generics for the identified ones of the substances 110A, 110B, 110N.

Alternatively or in addition, cost information retrieval logic 500 can compare the identified content and/or any possible generics to a data store of known cost data 142 to identify possible cost information associated with each of the different substances 110A, 110B, 110N and/or identified generic substances. The cost data can be provided in one or more forms. For instance, the cost data can be provided as cost per unit amount, cost per a certain quantity, etc. Further, the cost data can be provided as a range of prices or as an average, either nationally or in a geographical subset (e.g., region, state, county, city, etc.). Thereafter, a cost report 550 can be produced indicating any pricing information for the identified ones of the substances 110A, 110B, 110N and/or identified generic substances.

Figure 2:
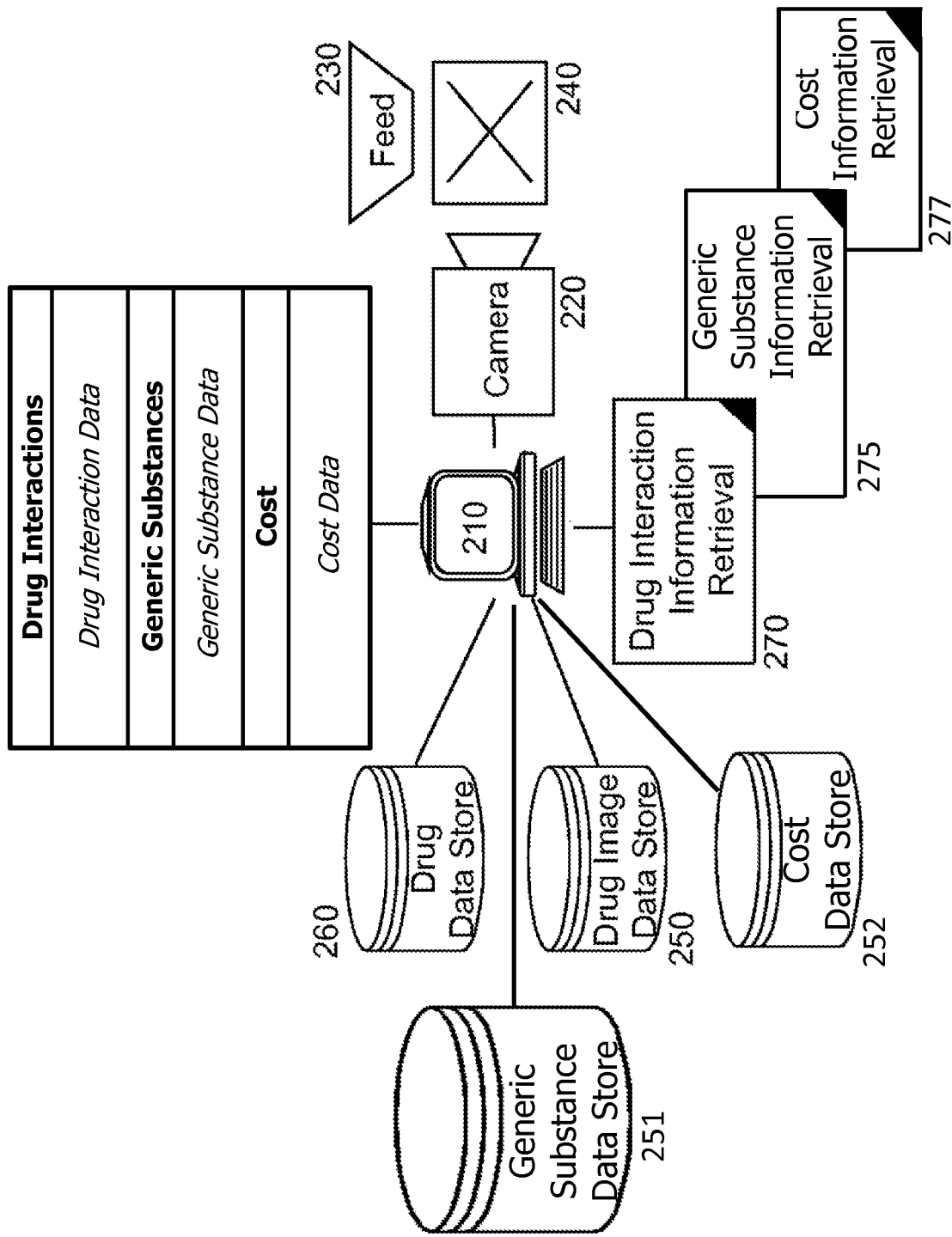
FIG. 2 is a schematic illustration of a data processing system configured for computer visualization of drugs for drug interaction, generic substance and/or cost information retrieval; and, FIG. 3 is a flow chart illustrating a process for computer visualization of drugs for drug interaction, generic substance and/or cost information retrieval.

The process shown in FIG. 1 can be implemented within a data processing system. In further illustration, FIG. 2 schematically depicts a data processing system configured for computer visualization of drugs for drug interaction information retrieval. The system can include a host computing platform 210 coupled to a camera 220 such as a digital still camera or digital video camera. In certain aspects of the disclosure, the host computing platform 210 can be a standalone computer. In other aspects of the disclosure, the host computing platform 210 is a mobile computing device. The camera 220 (either separate from the host computing platform 210 or integral thereto) can be focused on a marshalling point 240 provided by a marshalling apparatus 230, for example gravity feed or isolation chamber or miniature conveyor belt and/or a location in which the substances are disposed.

The host computing platform 210 also can be communicatively coupled a drug image data store 250 of known substances and corresponding known identifying content visually disposed on the known substances. This drug image data store 250 may reside within the host computing platform 210 and/or be located remote to the host computing platform 210.

The host computing platform 210 additionally can be communicatively coupled to a drug interaction data store 260 providing drug interaction data for different substances relative to other substances including prescription and over-the-counter drugs, vitamins and herbal remedies, and food products. This drug interaction store 260 may reside within the host computing platform 210 and/or be located remote to the host computing platform 210.

The host computing platform 210 additionally can be communicatively coupled to a generic substance data store 251 providing generic substance alternatives relative to other substances including prescription and over-the-counter drugs, vitamins and herbal remedies, and food products. This generic substance data store 251 may reside within the host computing platform 210 and/or be located remote to the host computing platform 210.

The host computing platform 210 additionally can be communicatively coupled to a cost data store 252 providing cost data for at least drugs and/or generic substances. The cost data store 252 can include cost data prescription and over-the-counter drugs, vitamins and herbal remedies, and food products. This cost data store 252 may reside within the host computing platform 210 and/or be located remote to the host computing platform 210.

The data store of drug image data, the data store of drug interaction data, the data store of generic substances data, and the data store of cost data can be disposed in a single database. Alternatively, one or more of these data stores can be disposed in a separate database.

Notably, the host computing platform 210 can support the execution of computer visualization for drug interaction information retrieval logic 270. The logic 270 can include program code enabled to acquire imagery of different substances in the marshalling point 240 or in another location imaged by the camera 220. The program code further can be enabled to locate and retrieve identifying content disposed on the different substances and to look up the identifying content in the drug image data store 250 in order to identify each of the substances. The program code yet further can be enabled to retrieve from drug interaction data store 260 drug interactions for each of the identified substances and to particularly correlate the retrieved drug interactions to different ones of the substances so that relative drug interactions can be determined for the substances. Finally, the program code can be enabled to render a report of drug interaction data in a graphical user interface display 280 of drug interaction data. The graphic user interface display 280 may be separate from the hosting computing platform 210 or integrated therewith, such as in a mobile device.

The host computing platform 210 can also support the execution of generic substance information retrieval logic 275. Once the identity of each of the substances is identified, the generic substance information retrieval logic 275 is configured to obtain generic alternatives, if available, for each of the identified substances. In so doing, the generic substance information retrieval logic 275 is configured to retrieve generic substance data from the generic substance data store 251. The generic substance information retrieval logic 275 is also configured to render a report in a graphical user interface display 280 of the generic alternatives of the identified substances.

The host computing platform 210 can also support the execution of cost information retrieval logic 277. Once the identity of each of the substances is identified and/or generic substance identified, the cost information retrieval logic 277 can be configured to obtain cost information, if available, for each of the identified substances and/or generic substances. In so doing, the cost information retrieval logic 277 can be configured to retrieve cost data from the cost data store 252. The cost information retrieval logic 277 is also configured to render a report in a graphical user interface display 280 of the cost of the identified substances and/or their generic alternatives.

It will be recognized by the skilled artisan that while the computer visualization for drug interaction information retrieval logic 270, the generic substance retrieval logic 275 and cost information retrieval logic 277 are shown to execute in a single host computing platform 210, the disclosure is not so limited and the logic 270, 275, 277 also can be distributed in form across multiple different computing platforms. Further, the camera 220 and marshalling apparatus 230 can be located remotely from the host computing platform 210 whilst providing acquired imagery to the host computing platform 210 over a computer communications network, whether wireless or wired. Yet further, one or more of the drug image data store 250, the drug interaction data store 260, the generic substance data store 251 and the cost data store 252 can be remotely disposed from the host computing platform 210 and accessible over a computer communications network, whether wireless or wired.

Figure 3:
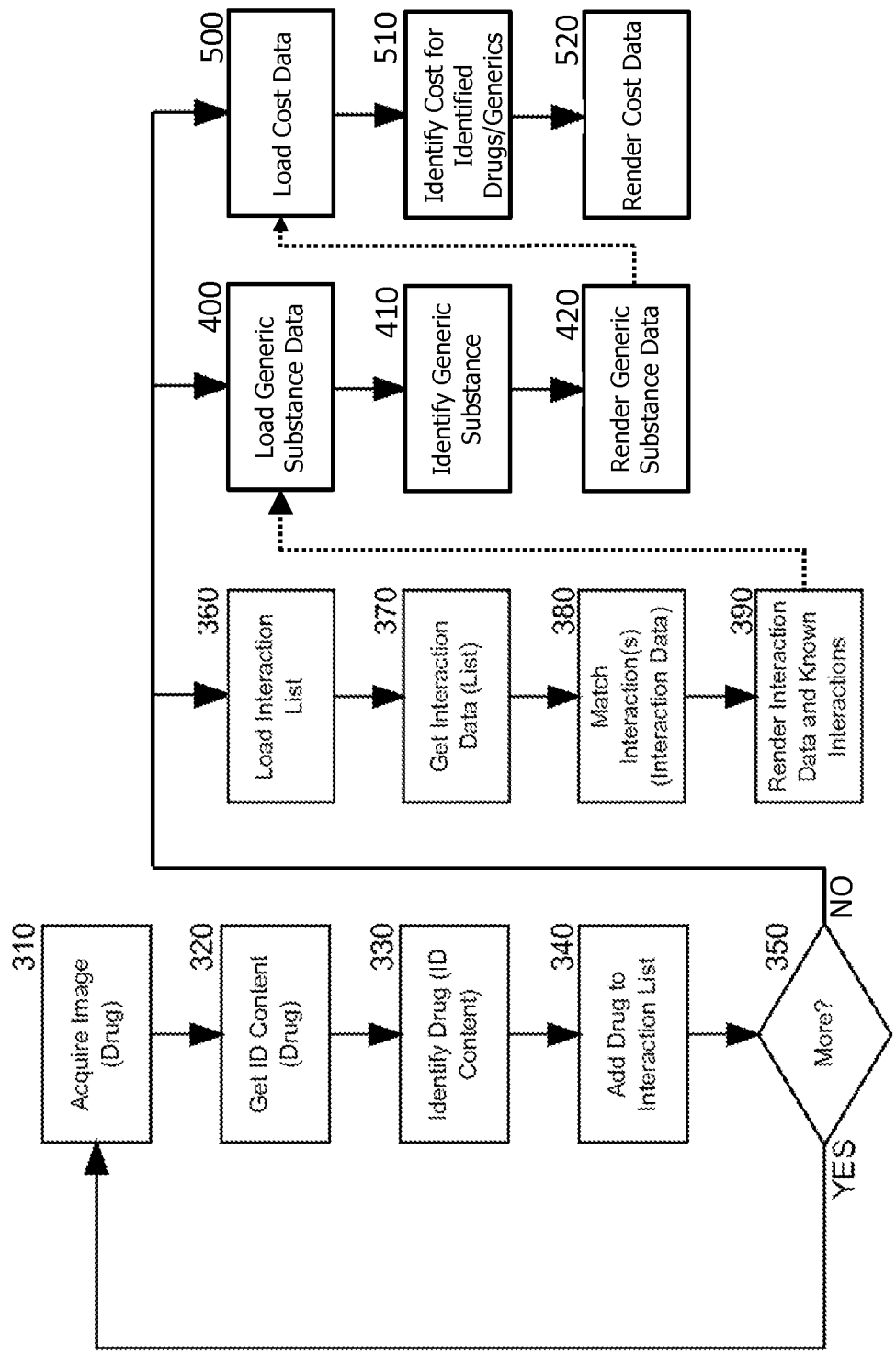

In yet further illustration of the operation of the computer visualization for drug interaction, generic substance and/or cost information retrieval logic 270, FIG. 3 is a flow chart illustrating a process for computer visualization of drugs for drug interaction, generic substance and/or cost information retrieval. Various possible steps of the process will now be described. However, it will be understood that the process may include other steps that are not shown here, and in fact, the process is not limited to including every step shown in FIG. 3. Further, the steps that are illustrated here as part of the process are not limited to any particular chronological order, either. Indeed, some of the steps may be performed in a different order than what is shown and/or at least some of the steps shown can occur simultaneously.

Beginning in block 310, an image of a substance such as a drug can be acquired and in block 320, identifying content for the substance can be retrieved from the image. In block 330, the substance can be identified according to the identifying content. In some embodiments, the user can be prompted to input whether the identification is correct. In block 340, the identified substance can be added to an interaction list. In decision block 350, if additional substances remain to be imaged, the process can repeat through block 310. Otherwise, the process can continue through block 360.

In block 360, the interaction list now populated by a list of imaged substances can be loaded for processing. In block 370, drug data and drug interaction data for each of the imaged substances in the list can be retrieved. Specifically, the drug data can include an expiration date for each of the imaged substances, usage instructions for each of the imaged substances, warnings provided if any for each of the imaged substances, contact information for a manufacturer of each of the imaged substances, a photograph or textual description of each of the imaged substances, as well as reorder information for each of the imaged substances.

In block 380, relative interactions between the different imaged substances can be determined by locating references in the interaction data for each of the imaged substances to others of the imaged substances. Finally, in block 390, the relative interactions can be rendered within a report such as a paper report or a graphical user interface display. Optionally, an activatable link can be provided in the display for selected ones of the imaged substances for reordering the selected ones of the imaged substances. In this way, the relative drug interactions resulting from the dispensing of multiple different substances can be determined without requiring a tedious manual process of looking up drug interaction data for each substance and manually correlating the drug interaction data for the specific combination of dispensed substances.

Either parallel to blocks 360-390 and/or in series (see dashed connecting lines) to blocks 360-390, generic substance data can be loaded in block 400. In block 410, any generic substances for the imaged substances can be identified. Next, the identity of the generic substances can be rendered within a report at block 420, such as a paper report or within a graphical user interface display. Either in parallel to and/or in series (see dashed connecting lines) to blocks 360-390 and/or blocks 410-400, cost data can be loaded in block 500. In block 510, the cost of the imaged substances and/or generic substances can be identified. In block 520, the cost of the imaged substances and/or generic substances can be rendered within a report, which can be a paper report or within a graphical user interface display.

In some embodiments, the process may be directed to providing only a subset of the information noted above. For instance, after an imaged substance is identified, the process may only be directed to identifying generic alternatives to the imaged substance and/or identifying cost information for the imaged substance. In such case, after a substance is identified in block 330 or after all substances are identified in block 350, the process can continue to block 400 and/or block 500.

Embodiments of the invention can take the form of an entirely hardware embodiment or an embodiment containing both hardware and software elements. In a certain aspects, the invention is implemented using software, which includes but is not limited to firmware, resident software, microcode, and the like. Furthermore, the invention can take the form of a computer program product accessible from a computer-usable or computer-readable storage medium providing program code for use by or in connection with a computer or any instruction execution system.

For the purposes of this description, a computer-usable or computer readable storage medium can be any apparatus or device that can contain or store the program for use by or in connection with the instruction execution system, apparatus, or device. Examples of a computer-readable medium include a semiconductor or solid state memory, magnetic tape, a removable computer diskette, a random access memory (RAM), a read-only memory (ROM), a rigid magnetic disk and an optical disk. Examples of optical disks include compact disk-read only memory (CD-ROM), compact disk-read/write (CD-R/W) and DVD.

Aspects herein can be embodied in other forms without departing from the spirit or essential attributes thereof. Accordingly, reference should be made to the following claims, rather than to the foregoing specification, as indicating the scope of the invention.

What is claimed is:

1. A computer-implemented method for computer visualization of drugs for drug interaction, generic substance information retrieval and drug pricing information retrieval, comprising:
   receiving, via a marshalling apparatus, a plurality of different substances and isolating, via the marshalling apparatus, individual ones of the different substances for imaging by a camera and defining a marshalling point, wherein the camera is positioned to focus on the marshalling point;
   using a processor communicatively coupled to a data store of drug image data, a data store of generic substance data, a data store of drug interaction, and a data store of pricing information for brand name drugs and generic substances, wherein the processor is configured to:
   acquire, for each of the plurality of different substances and using the camera, images of at least one external characteristic of a physical body of the substance;
   determine an identity of each of the plurality of different substances based upon the at least one external characteristic from the acquired images;
   retrieve drug interaction data for each of the plurality of different substances using the determined identities;
   retrieve pricing information for each of the plurality of different substances based upon the determined identities;
   correlate drug interaction data for at least one of the plurality of different substances with at least one other of the plurality of different substances;
   retrieve generic substance data for each of the plurality of different substances using the determined identities;
   identify at least one generic substance of at least one of the plurality of different substances;
   determine a price comparison between the identified generic substance and a brand name drug equivalent, and
   simultaneously display the correlated drug interaction data, the at least one generic substance and the price comparison.

2. The method of claim 1, wherein the method is performed using a mobile computing device.

3. The method of claim 1, wherein the at least one external characteristic includes a pill marking or code.

4. The method of claim 1, wherein the substances comprise at least one drug.

5. The method of claim 1, wherein the data store of drug image data, the data store of drug interaction data, the data store of generic substance data and the data store of pricing information for brand name drugs and generic substances are disposed in a single database.

6. The method of claim 1, wherein the marshalling apparatus comprises a gravity feed.

7. The method of claim 1, wherein the marshalling apparatus comprises a conveyor belt.

8. The method of claim 1, wherein the marshalling apparatus comprises a chamber.

9. The method of claim 1, wherein the pricing information is displayed as cost per unit amount or cost per quantity.

10. The method of claim 1, wherein the pricing information is displayed as a range of prices or as an average, either nationally or in a geographical subset.

* * * * *